United States Patent [19]

Finlayson

[11] 4,116,866

[45] Sep. 26, 1978

[54] ORGANOPHILIC CLAY GELLANT

[75] Inventor: Claude Malcolm Finlayson, Houston, Tex.

[73] Assignee: N L Industries, Inc., New York, N.Y.

[21] Appl. No.: 812,099

[22] Filed: Jul. 1, 1977

[51] Int. Cl.$^2$ ............................................. B01J 13/00
[52] U.S. Cl. .................................. 252/316; 106/38.7; 252/28; 424/357
[58] Field of Search ................................... 252/316, 28

[56] References Cited

U.S. PATENT DOCUMENTS

| | | | |
|---|---|---|---|
| 2,531,427 | 11/1950 | Hauser | 252/3 16 X |
| 2,554,222 | 5/1951 | Stross | 252/28 |
| 2,623,852 | 12/1952 | Peterson | 252/28 |
| 2,677,661 | 5/1954 | O'Halloran | 252/49.6 |
| 2,966,506 | 12/1960 | Jordan | 260/448 C |

*Primary Examiner*—Richard D. Lovering
*Attorney, Agent, or Firm*—Malcolm L. Sutherland

[57] ABSTRACT

An organophilic clay gellant having enhanced utility in alcohol compositions is prepared from the reaction product of a smectite-type clay having a cation exchange capacity of at least 0.75 milliequivalents per gram and from about 0.90 to less than about 1.20 milliequivalents per gram of clay of a castor fatty propylamido benzyl dialkyl, i.e., methyl or ethyl ammonium salt.

9 Claims, No Drawings

ORGANOPHILIC CLAY GELLANT

This invention relates to organophilic organic-clay complexes which are dispersible in organic liquids to form a gel therein. Such compositions are particularly suitable for forming gels with alcohol compositions and for use in foundry molding sand binders, cosmetics and the like.

It is well known that organic compounds which contain a cation will react under favorable conditions by ion-exchange with clays which contain a negative layer-lattice and exchangeable cations to form organophilic organic-clay products. If the organic cation contains at least one alkyl group containing at least 10 carbon atoms, then such organoclays have the property of swelling in certain organic liquids. See for example U.S. Pat. No. 2,531,427 and U.S. Pat. No. 2,966,506, both incorporated herein by reference, and the book *Clay Mineralogy*, 2nd Edition, 1968 by Ralph E. Grim (McGraw-Hill Book Co., Inc.), particularly Chapter 10, "Clay-Mineral-Organic Reactions"; pages 356 to 368; "Ionic Reactions, Smectite"; and pages 392 to 401; "Organophilic Clay-Mineral Complexes".

Since the commercial introduction of these organoclays in the early 1950's (trademarked BENTONE), it has become well known to gain the maximum gelling (thickening) efficiency from these organoclays by adding a low molecular weight polar organic material to the composition. Such polar organic materials have been variously called dispersants, dispersion aids, solvating agents, dispersion agents and the like. See for example the following U.S. Pat. Nos.: O'Halloran 2,677,661; McCarthy et al. 2,704,276; Stratton 2,833,720; Stratton 2,879,229; Stansfield et al. 3,294,683. Articles which disclose the use of organophilic clay gellants and polar organic dispersants as viscosifiers in organic systems are the following: (1) "Some Aspects of BENTONE Greases", R. E. Fariss, NLGI Spokesman, January, 1957, pages 10 to 16; (2) "A Modified Clay Thickener for Lubricating Fluids", R. E. Fariss, NLGI Spokesman, February, 1960, pages 432 to 437; (3) "A Modified Clay Thickener for Corrosion Resistant Greases", R. F. House, NLGI Spokesman, April, 1966, pages 11 to 17; (4) "The Gelation of Hydrocarbons by Montmorillonite Organic Complexes", W. T. Granquist and James L. McAtee, Jr., J. Colloid Science 18, 409 to 420 (1963); (5) "Flow Properties of Dispersions of an Organo-Montmorillonite in Organic Media", J. V. Kennedy and W. T. Granquist, NLGI Spokesman, August, 1965, pages 138 to 145; (6) "Some Fundamental Aspects of the Permeability of Organo-Montmorillonite Greases", J. L. McAtee, Jr. and Liang-koa Chen, NLGI Spokesman, June, 1968, pages 89 to 95; (7) "Fundemental Aspects of the Permeability of Gel Strength of Inorganic Thickened Greases", J. L. McAtee, Jr. and J. P. Freeman, NLGI Spokesman, September, 1968, pages 200 to 205; (8) "Study of Dispersants in the Preparation of Inorganic Thickened Greases", J. L. McAtee, Jr., NLGI Spokesman, May, 1969, pages 52 to 60; (9) "Extent of Dispersion of an Organo-Clay Complex in Oil-an Infrared Method", F. W. Schaefer, A. C. Wright and W. T. Granquist, NLGI Spokesman, March, 1971, pages 418 to 423.

Although the use of such gellants, as the commercially available BENTONE's and BARAGEL's, has been known for some time, heretofore the amount of gellant required to produce a satisfactory gel with alcohol compositions has been very large and uneconomic. Accordingly, these gellants have not been used commercially with alcohol compositions and many industries, e.g., the cosmetic and foundry industries, continued to have a need for an efficient alcohol gellant which is not met by any presently known product. Accordingly, it is an object of this invention to provide an organophilic clay gellant which is easy to disperse in alcohol systems for gelling alcohol systems when used in relatively small amounts.

An organophilic clay gellant having enhanced dispersibility and gelling properties in alcohol systems has been unexpectedly discovered comprising the reaction product of a castor-fatty propylamido benzyl dialkyl ammonium compound, and a smectite-type clay having a cation exchange capacity of at least about 75 milliequivalents per 100 grams of said clay, and wherein the amount of said ammonium compound is from about 90 to about 120 milliequivalents per 100 grams of said clay, 100% active clay basis.

The clays used to prepare the organoclay thickeners of this invention are smectite-type clays which have a cation exchange capacity of at least 75 milliequivalents per 100 grams of clay. Particularly desirable types of clay are the naturally occurring Wyoming variety of swelling bentonite and like clays, and hectorite, a swelling magnesium-lithium silicate clay.

The clays, especially the bentonite type clays, are preferably converted to the sodium form if they are not already in this form. This can conveniently be done by preparing an aqueous clay slurry and passing the slurry through a bed of cation exchange resin in the sodium form. Alternatively the clay can be mixed with water and a soluble sodium compound such as sodium carbonate, sodium hydroxide, etc., and shearing the mixture such as with a pugmill or extruder.

Smectite-type clays prepared synthetically by either a pneumatolytic or, preferably, a hydrothermal synthesis process can also be used to prepare these novel organic-clay complexes. Representative of such clays are the following:

Montmorillonite: $[(Al_{4-x}Mg_x) Si_8O_{20}(OH)_{4-f}F_f] \; x \; R+$
where $0.55 \leq x \leq 1.10, f \leq 4$ and R is selected from the group consisting of Na, Li, NH$_4$, and mixtures thereof;

Bentonite: $[(Al_{4-x}Mg_x)(Si_{8-y}Al_y)O_{20}(OH)_{4-f}F_f] \; (x+y) \; R+$
where $0 < x < 1.10, \; 0 < y < 1.10, \; 0.55 \leq (x+y) \leq 1.10, \; f \leq 4$ and R is selected from the group consisting of Na, Li, NH$_4$, and mixtures thereof;

Beidellite: $[(Al_{4+y}) (Si_{8-x-y}Al_{x+y})O_{20}(OH)_{4-f}F_f] \; x \; R+$
where $0.55 \leq x \leq 1.10, \; 0 \leq y \leq 0.44, \; f \leq 4$ and R is selected from the group consisting of Na, Li, NH$_4$ and mixtures thereof;

Hectorite: $[(Mg_{6-x}Li_x) Si_8O_{20} (OH)_{4-f}F_f] \; x \; R+$ where $0.57 \leq x \leq 1.15, f \leq 4$ and R is selected from the group consisting of Na, Li, NH$_4$, and mixtures thereof;

Saponite: $[(Mg_{6-y}Al_y) (Si_{8-x-y}Al_{x+y})O_{20}(OH)_{4-f}F_f] \; x \; R+$
where $0.58 \leq x \leq 1.18, \; 0 \leq y \leq 0.66, f \leq 4$ and R is selected from the group consisting of Na, Li, NH$_4$, and mixtures thereof;

Stevensite: $[(Mg_{6-x}) Si_8O_{20}(OH)_{4-f}F_f] \; 2 \; x \; R+$ where $0.28 \leq x \leq 0.57, f \leq 4$ and R is selected from the group consisting of Na, Li, NH$_4$ and mixtures thereof.

These clays may be synthesized hydrothermally by forming an aqueous reaction mixture in the form of a slurry containing mixed hydrous oxides or hydroxides of the desired metals with or without, as the case may be, sodium (or alternate exchangeable cation or mixture thereof) fluoride in the proportions defined by the above formulas and the preselected values of $x$, $y$, and $f$ for the particular synthetic smectite desired. The slurry is then placed in an autoclave and heated under autogenous pressure to a temperature within the range of approximately 100° to 325° C., preferably 275° to 300° C., for a sufficient period of time to form the desired product. Formation times of 3 to 48 hours are typical at 300° C., depending on the particular smectite being synthesized, and the optimum time can readily be determined by pilot trials. Representative hydrothermal processes for preparing synthetic smectites are described in the following U.S. Pat. Nos., incorporated herein by reference: Granquist 3,252,757; Neumann 3,586,478; Orlemann 3,666,407; Neumann 3,671,190; Hickson 3,844,978; Hickson 3,844,979; Granquist 3,852,405; Granquist 3,855,147.

The cation exchange capacity of the smectite clay can be determined by the well-known ammonium acetate method.

The organic compounds useful in the practice of this invention are quaternary ammonium salts containing two methyl or ethyl radicals, one benzyl radical, and a radical which is a castor based fatty acid substituted propylamido radical. The salt anion is preferably selected from the group consisting of chloride and bromide, and mixtures thereof, and is more preferably chloride, although other anions such as acetate, hydroxide, nitrite, etc., may be present in the quaternary ammonium salt to neutralize the quaternary ammonium cation. The methyl benzyl dialkyl ammonium salt may be represented by the formula:

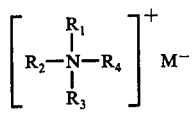

where $R_1$ and $R_4$ are alkyl of about 1 to 3 carbon atoms, e.g. methyl or ethyl; $R_3$ is benzyl; and $R_4$ is hydroxystearyl propylamido, rincinoleyl propylamido, ethoxylated hydroxystearyl propylamido, or ethoxylated rincinoleyl propylamido; and where $M^-$ is preferably selected from the group consisting of $Cl^-$, $Br^-$, $NO_2^-$, $OH^-$, $C_2H_3O_2^-$, and mixtures thereof.

The preferred quaternary amine for use in the practice of this invention has the general structure

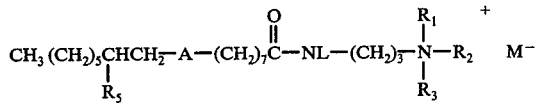

where $R_1$, $R_2$, $R_3$ and M have the above meaning; $R_5$ is hydroxyl or $-OCH_2CH_2OH$; and A is $-CH_2CH_2-$ or $-CH=CH-$. Typical preferred quaternary amines are γ-(12-hydroxy-stearamido) propyl-dimethyl benzyl ammonium chloride; γ-(12-hydroxy-oleylamido) propyl-dimethyl benzyl ammonium chloride; γ-(12-(2-hydroxyethyloxy)oleylamido) propyl dimethyl benzyl ammonium chloride; and γ-(12-hydroxy-stearamido) propyl diethyl benzyl ammonium chloride.

Many processes are known to prepare ammonium salts. The salts used in this invention can be prepared by reacting the appropriate amine and acid to produce the amido-amine intermediate as illustrated by the reaction:

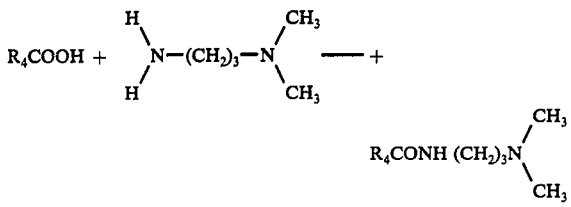

where $R_4$ has the above meaning. The product of this reaction is then quaternized with, for example, benzyl chloride. It is generally preferred to carry out the reaction in the presence of a solvent such as propylene glycol or isopropanol. Although various amounts of solvent can be employed, about 70 to 75% solids by weight is type preferred. The reaction can be carried out at various temperatures; however, temperatures of about 50° to 90° C. are satisfactory.

The organophilic clay gellants of this invention can be prepared by admixing the clay, quaternary ammonium compound and water together, preferably at a temperature within the range from about 35° C. to about 85° C., more preferably about 60° C. to about 80° C. for a period of time sufficient for the organic compound to coat the clay particles, followed by filtering, washing, drying, and grinding. In using the organophilic clay gellants in emulsions, the drying and grinding steps may be eliminated. When admixing the clay, quaternary ammonium compound and water together in such concentrations that a slurry is not formed, then the filtration and washing steps can be eliminated.

Preferably, the clay is dispersed in water at a concentration from about 3% to 7%; the slurry optionally centrifuged to remove non-clay impurities which can constitute about 10% to about 50% of the starting clay composition; the slurry agitated and heated to a temperature in the range from 140° F. (60° C.) to 170° F. (77° C.); the quaternary amine salt added in the desired milliequivalent ratio, preferably as a liquid in isopropanol or dispersed in water; and the agitation continued to effect the reaction.

The amount of the ammonium salt added to the clay for purposes of this invention must be sufficient to impart to the organophilic clay the characteristics desired. The milliequivalent ratio is defined as the number of milliequivalents of the organic compound in the organoclay per 100 grams of clay, 100% active clay basis. Generally, the organophilic clays of this invention have a milliequivalent ratio from about 90 to 120, and preferably about 95 to 115. At lower milliequivalent ratios, the organophilic clays produced are not as effective gellants. At higher milliequivalent ratios, the organophilic clays are poor gellants. However, it will be recognized that the preferred milliequivalent within the range from 90 or 95 to 115 or 120, will vary depending on the characteristics of the organic system to be gelled by the organophilic clay.

The following examples illustrate the gellants of this invention and the benefits afforded through the utilization thereof but are not to be construed as limiting the invention except as discussed herein.

The smectite clays used are hectorite and Wyoming bentonite. The hectorite clay was slurried in water and centrifuged to remove essentially all of the non-clay impurities. The Wyoming bentonite clay was slurried in water, centrifuged to remove essentially all of the non-clay impurities, and ion-exchanged to the sodium form by passing the slurry through a bed of cation exchange resin in the sodium form. Two commercially available gellants were used for comparison. BARAGEL and BENTONE are Wyoming bentonite and hectorite, respectively, reacted with benzyl dimethyl hydrogenated tallow ammonium chloride. These gellants are available in a number of milliequivalent ratios.

The gellants of this invention produce a desired viscosity in an alcohol system when used in a lesser amount than these commercial gellants.

The data set forth in the examples is derived from a high-shear test and a moderate, or low-shear test. In the high-shear test, gels were prepared in Everclear (95% grain alcohol, 5% water) by adding the gellant to the Everclear in a Waring Blender over a 15 second period at a Variac setting of 40 volts. The speed was increased to 15,000 RPM (Variac setting, 119 volts) for 6 minutes. The resulting gel was cooled by water for 30 to 90 minutes. The sample was then spatulated 1 minute and measured on the Brookfield Viscometer at 10, 20, 50, and 100 RPM. Batch size was 300 gm total. The relative efficiency of the gellant is defined as the concentration of gellant required to produce a viscosity of 1000 centipoises at 50 RPM. To determine the relative efficiency, a series of samples of varying concentrations are run.

For the moderate-shear test procedure, gels were prepared in Everclear at 10% concentration of gellant using the Dispersator at 5900 RPM. Batch size was 300 gm total. Initially, 15 gm of gellant were added to 270 gm of Everclear at low speed. The speed was increased to 5900 RPM for 5 minutes. An additional 15 gm of gellant was added at slow speed and the speed increased to 5900 RPM for an additional 5 minutes. The samples were water cooled for 30 to 90 minutes, given a 1 minute spatulation and viscosities determined on the Brookfield Viscometer at 10, 20, 50, and 100 RPM.

EXAMPLE 1

The organophilic clay gellants were prepared by heating a clay slurry to a temperature within the range from 150° F. (66° C.) to 170° F. (77° C.), adding while stirring the clay slurry and indicated quaternary ammonium salt, and continuing the stirring for approximately 45 minutes, followed by filtering, washing, drying at 140° F. (60° C.) and grinding. A number of gellants containing various concentrations of the organic were prepared and the relative efficiencies of the gellants were determined as described above. Table I lists the gellants tested and their relative efficiency.

TABLE I

| GELLANT | CLAY | ORGANIC | ME | RELATIVE EFFICIENCY |
|---|---|---|---|---|
| 1 | Wyoming Bentonite | γ-(12-hydroxy-stearamido)propyl-dimethyl-benzyl-amonium chloride (Organic A) | 109.3 | 5.1% |
| 2 | Wyoming Bentonite | γ-(12-hydroxy-oleylamido)propyl-dimethyl-benzyl-ammonium chloride (Organic B) | 108.2 | 5.4% |
| 3 | Wyoming Bentonite | γ-(12-hydroxy-stearamido)propyl-diethyl-benzyl-ammonium chloride (Organic C) | 106.5 | 5.8% |
| 4 | Wyoming Bentonite | γ-(12-hydroxyethyloxyoleylamido)propyl-dimethyl-benzyl-ammonium chloride (Organic D) | 112.5 | 6.25% |
| 5 | BARAGEL 24 | (Wyoming bentonite reacted with benzyl dimethyl hydrogenated tallow ammonium chloride) | 109.3 | 6.1% |
| 6 | BARAGEL 24 | | 95.3 | 6.4% |
| 7 | BARAGEL 24 | | 100–104 (commercial range) | 8.8% (est.) |
| 8 | HECTORITE | Organic D | 100.5 | 5.75% |
| 9 | HECTORITE | Organic A | 112.7 | 6.0% |
| 10 | BENTONE 27 | (Hectorite reacted with benzyl dimethyl hydrogenated tallow ammonium cloride) | 95.9 | 6.3% |
| 11 | BENTONE 27 | | 107.5 | 6.3% |
| 12 | BENTONE 27 | | 96–101 (commercial range) | 11.0% |

CABOSIL M-5 produced no gel at 25% concentration under this test. The relative efficiencies of the gellants in accordance with this invention, Gellant Nos. 1 through 4, 8 and 9, compared to the efficiencies of the commercial BARAGEL and BENTONE gellants (Nos. 5 through 7, 10, 11, and 12) demonstrate the effectiveness of the gellants of this invention. Gellant No. 8 is also more efficient than Gellant No. 10 under the moderate-shear test as shown by the data of Table II. Concentrations were 10%.

TABLE II

| | BROOKFIELD-CENTIPOISES | | | |
|---|---|---|---|---|
| GELLANT | 10 RPM | 20 RPM | 50 RPM | 100 RPM |
| 8 | 8300 | 4390 | 1920 | 1010 |
| 10 | 2400 | 1250 | 550 | 305 |

Tests were also run using Gellant No. 8 to demonstrate the effect of the ME ratio. The speed used in preparing the gell in these tests was 13,000 RPM, rather than 15,000 RPM, and 7% concentration of gellant was used. Table III provides the data.

TABLE III

| | BROOKFIELD-CENTIPOISE | | | |
|---|---|---|---|---|
| ME | 10 RPM | 20 RPM | 50 RPM | 100 RPM |
| 90.2 | 6700 | 2530 | 1550 | 835 |
| 102.5 | 6100 | 3265 | 1450 | 798 |
| 108.3 | 5700 | 3000 | 1310 | 717 |
| 119.2 | 2620 | 1395 | 614 | 338 |

A number of gellants were tested in 95% grain alcohol. The gels were remeasured after storage for several weeks to determine the effect of aging. The data is summarized in Table IV.

TABLE IV

| Gellant No. | Concentration % | Brookfield RPM | Original | 7 Week | 8 Week | 10 Week |
|---|---|---|---|---|---|---|
| 5 | 5½ | 10 | 3200 | 2710 | | |
| | | 20 | 1625 | 1400 | | |
| | | 50 | 680 | 610 | | |
| | | 100 | 364 | 328 | | |
| 5 | 7 | 10 | 6350 | 6050 | | |
| | | 20 | 3300 | 3150 | | |
| | | 50 | 1340 | 1320 | | |
| | | 100 | 690 | 700 | | |
| 10 | 7 | 10 | 5560 | | 5000 | |
| | | 20 | 2925 | | 2625 | |
| | | 50 | 1290 | | 1176 | |
| | | 100 | 690 | | 635 | |
| 1 | 5½ | 10 | 6000 | | | 4900 |
| | | 20 | 2975 | | | 2550 |
| | | 50 | 1210 | | | 1100 |
| | | 100 | 642 | | | 593 |
| 2 | 5½ | 10 | 2920 | | | 3880 |
| | | 20 | 2480 | | | 2150 |
| | | 50 | 1028 | | | 900 |
| | | 100 | 540 | | | 490 |
| 4 | 6½ | 10 | 5420 | | | 4170 |
| | | 20 | 2710 | | | 2230 |
| | | 50 | 1096 | | | 940 |
| | | 100 | 570 | | | 515 |
| 3 | 6½ | 10 | 5340 | | | 4500 |
| | | 20 | 2575 | | | 2340 |
| | | 50 | 1062 | | | 1000 |
| | | 100 | 556 | | | 594 |
| 8 | 7 | 10 | 5700 | | | 5100 |
| | | 20 | 3000 | | | 2725 |
| | | 50 | 1310 | | | 1200 |
| | | 100 | 717 | | | 655 |

EXAMPLE 2

Comparative efficiencies of gels prepared from gellants made with Organic A with other BENTONE and BARAGEL products were obtained in a 95/5 Ethacol/water system and are given below in Table V.

EXAMPLE 3

Gellants prepared by reacting ammonium bromide and nitrites having the same organic structure as Organics A, B, C, and D with Wyoming bentonite and hectorite are effective gellants in alcohol systems when prepared in accordance with this invention. Additionally, γ-(12-(2-hydroxyethyloxy)oleylamido)propyl-diethyl-benzyl ammonium chloride and γ-(12-hydroxy-oleylamido)propyl-diethyl-benzyl ammonium chloride when reacted with natural and synthetic bentonites and hectorites produce effective gellants.

TABLE V

| GELLANT | ME | RELATIVE EFFICIENCY (%) |
|---|---|---|
| Wyoming Bentonite & Organic A | 104.5 | 4.8 |
| HECTORITE & Organic A | 105 | 5.2 |
| Wyoming Bentonite & Organic A | 111.4 | 5.3 |
| BENTONE 27 | 106 | 6.3 |
| BENTONE 27 | 99 | 6.9 |
| BENTONE 27 | 101 | 7.3 |
| BARAGEL 24 | 100–104 (commercial range) | 8.4 |
| BARAGEL 35 | 108–114 (commercial range) | 10.4 |
| BENTONE 38 | 92–98 | 15.2 |
| BENTONE 38 | 92–98 (commercial range) | 18.1 |

The examples indicate the remarkable results achieved utilizing the process of this invention, namely, that the viscosity of organic alcohol systems is efficiently increased with an organophilic clay gellant of the type claimed when the organophilic clay gellant has a milliequivalent ratio within the range of about 90 to about 120.

The invention being thus described, it will be obvious that the same may be varied in many ways, such variations are not to be regarded as a departure from the spirit and scope of the invention, and all such modifications are intended to be included within the scope of the following claims.

What is claimed is:

1. An organophilic clay gellant comprising the reaction product of a castor-fatty propylamido benzyl dialkyl ammonium compound wherein the alkyls are of about 1 to 3 carbon atoms and a smectite-type clay having a cation exchange capacity of at least 75 milliequivalents per 100 grams of said clay, and wherein the amount of said ammonium compound is from about 90 to about 120 milliequivalents per 100 grams of said clay, 100% active clay basis.

2. The composition of claim 1 wherein the smectite-type clay is selected from the group consisting of hectorite and sodium bentonite.

3. The composition of claim 1 wherein the smectite-type clay contains from about 10% to about 50% non-clay impurities.

4. An organophilic clay gellant comprising the reaction product of a castor-fatty propylamido benzyl dialkyl ammonium compound and a smectite-type clay having a cation exchange capacity of at least 75 milliequivalents per 100 grams of said clay, wherein the ammonium compound has the general formula:

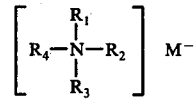

wherein: $R_1$ and $R_2$ are alkyl of about 1 to 3 carbon atoms; $R_3$ is benzyl; $R_4$ is selected from the group consisting of hydroxy-stearyl propylamido, rincinoleyl propylamido, ethoxylated hydroxystearyl propylamido and ethoxylated rincinoleyl propylamido; and M is selected from the group consisting of $Cl^-$, $Br^-$, $NO_2^-$, $OH^-$, and $C_2H_3O_2^-$, and wherein the amount of said ammonium compound is from about 90 to about 120 milliequivalents per 100 grams of said clay, 100% active clay basis.

5. An organophilic clay gellant having enhanced dispersibility in organic systems comprising the reaction product of an ammonium compound having the formula:

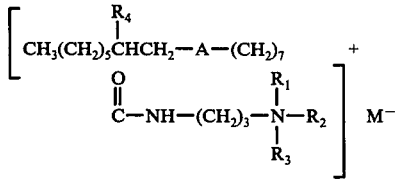

wherein: $R_1$ and $R_2$ are alkyl of 1 to 3 carbon atoms, $R_3$ is benzyl, $R_4$ is selected from the group consisting of hydroxyl and $OCH_2CH_2OH$, A is selected from the group consisting of $-CH_2CH_2-$ and $-CH=CH-$ and where $M^-$ is selected from the group consisting of $Cl^-$, $Br^-$, $NO_2^-$, $OH^-$, and $C_2H_3O_2^-$, and a smectite-type clay selected from the group consisting of hectorite and sodium bentonite, and wherein the amount of said ammonium compound is from about 90 to about 120 milliequivalents per 100 grams of said clay, 100% active clay basis.

6. The composition of claim 5 wherein the ammonium compound is γ-(12-hydroxy-stearamido)propyl-dimethyl-benzyl ammonium chloride.

7. The composition of claim 5 wherein the ammonium compound is γ-(12-hydroxy-oleylamido)propyl-dimethyl-benzyl ammonium chloride.

8. The composition of claim 5 wherein the ammonium compound is γ-(12-(2-hydroxyethyloxy)oleylamido) propyl-dimethyl-benzyl ammonium chloride.

9. The composition of claim 5 wherein the ammonium compound is γ-(12-hydroxy-stearamido)propyl-diethyl-benzyl ammonium chloride.

* * * * *